(12) United States Patent
Monnoyer et al.

(10) Patent No.: US 8,061,185 B2
(45) Date of Patent: Nov. 22, 2011

(54) METHOD FOR TESTING A SLURRY USED TO FORM A SEMICONDUCTOR DEVICE

(75) Inventors: Philippe Monnoyer, Grenoble (FR); Janos Farkas, Saint Ismier (FR); Farid Sebaai, Saint Martin d'Heres (FR)

(73) Assignee: Freescale Semiconductor, Inc., Austin, TX (US)

( * ) Notice: Subject to any disclaimer, the term of this patent is extended or adjusted under 35 U.S.C. 154(b) by 641 days.

(21) Appl. No.: 12/091,693

(22) PCT Filed: Oct. 25, 2005

(86) PCT No.: PCT/EP2005/013519
§ 371 (c)(1),
(2), (4) Date: Apr. 25, 2008

(87) PCT Pub. No.: WO2007/048441
PCT Pub. Date: May 3, 2007

(65) Prior Publication Data
US 2008/0282778 A1   Nov. 20, 2008

(51) Int. Cl.
*G01N 29/04* (2006.01)
*G01N 29/28* (2006.01)
(52) U.S. Cl. .............. 73/61.42; 73/61.59; 73/61.62; 73/61.65
(58) Field of Classification Search ............ 73/61.42, 73/61.59, 61.62, 61.65, 863, 864, 864.51, 73/864.81–864.83, 864.91
See application file for complete search history.

(56) References Cited

U.S. PATENT DOCUMENTS

| | | | |
|---|---|---|---|
| 5,078,965 A * | 1/1992 | Pearson | 422/3 |
| 5,404,906 A | 4/1995 | Aoshima et al. | |
| 5,481,059 A * | 1/1996 | Brock et al. | 585/866 |
| 5,569,844 A * | 10/1996 | Sowerby | 73/61.75 |
| 5,710,069 A * | 1/1998 | Farkas et al. | 438/7 |
| 5,733,819 A * | 3/1998 | Kodama et al. | 438/692 |
| 5,846,398 A | 12/1998 | Carpio | |
| 6,109,098 A * | 8/2000 | Dukhin et al. | 73/64.42 |
| 6,246,474 B1 * | 6/2001 | Cerni et al. | 356/335 |
| 6,447,373 B1 * | 9/2002 | Lack et al. | 451/41 |
| 6,617,070 B1 * | 9/2003 | Morrissey et al. | 429/105 |
| 6,790,127 B2 * | 9/2004 | Tanoue et al. | 451/41 |
| 6,930,777 B1 * | 8/2005 | Sevick-Muraca et al. | 356/336 |

(Continued)

FOREIGN PATENT DOCUMENTS

WO   9956106 A1   11/1999

(Continued)

OTHER PUBLICATIONS

"Acoustics and Electroacoustics for Ceramics", Dispersion Technology, Inc., Mar. 1999.*

(Continued)

*Primary Examiner* — David A. Rogers

(57) ABSTRACT

A method for forming a semiconductor device, the method includes providing a semiconductor substrate, applying a slurry to the semiconductor substrate, wherein the slurry was tested using a testing method includes taking a first undiluted sample from a top of the slurry; determining a first particle size distribution characteristic of the first undiluted sample; taking a second undiluted sample from a bottom of the slurry; determining a second particle size distribution characteristic of the second undiluted sample; and comparing a difference between the first particle size distribution characteristic and the second particle size distribution characteristics with a first predetermined value.

20 Claims, 4 Drawing Sheets

U.S. PATENT DOCUMENTS

| | | | |
|---|---|---|---|
| 2003/0124858 A1* | 7/2003 | Nakabayashi et al. | 438/692 |
| 2004/0072439 A1* | 4/2004 | Small et al. | 438/694 |
| 2004/0182138 A1* | 9/2004 | Greenwood et al. | 73/53.03 |
| 2004/0198183 A1* | 10/2004 | Moore et al. | 451/5 |
| 2005/0073681 A1* | 4/2005 | Sevick-Muraca et al. | 356/336 |
| 2005/0198912 A1* | 9/2005 | Kim et al. | 51/307 |
| 2007/0081931 A1* | 4/2007 | Cho et al. | 423/21.1 |
| 2007/0169421 A1* | 7/2007 | Koyama et al. | 51/298 |

FOREIGN PATENT DOCUMENTS

| | | |
|---|---|---|
| WO | 03016881 A2 | 2/2003 |

OTHER PUBLICATIONS

Dukhin et al; "Characterization of Chemical Polishing Materials by means of Acoustic Spectroscopy"; Dec. 1998, www.dispersion.com.

"Characterization of CMP Slurries"; Feb. 2003, www.dispersion.com.

* cited by examiner

US 8,061,185 B2

METHOD FOR TESTING A SLURRY USED TO FORM A SEMICONDUCTOR DEVICE

FIELD OF THE INVENTION

This invention relates generally to forming semiconductor devices, and more specifically, to methods for testing a slurry used to manufacture semiconductor devices.

BACKGROUND OF THE INVENTION

Chemical mechanical polishing (CMP) is a conventional process used in the semiconductor industry to planarize a layer formed on a semiconductor substrate. During CMP, a polishing pad and slurry are placed in contact with the layer to be polished and the polishing pad rotates relative to the wafer. It is important that the slurry used is homogenous and of good quality. For example, if slurry particles aggregate while the polishing pad rotates the slurry particles may scratch the layer being polished and also cause residual particles and other surface defects.

To avoid defectivity problems a semiconductor manufacturer wants to make sure the slurry quality is meeting the CMP requirements. This means the slurry must be colloidaly stable or it cannot contain large aggregates resulting from its particles aggregation. Current analysis of the slurry involves incorrect or costly test methods. For example, the testing may be performed on a diluted slurry sample. Because the sample is diluted no aggregation is detected. However, the slurry may have aggregate problems when it is undiluted. The dilution of a slurry changes its concentration in electrolytes and increases the electrical double layer thickness around the particles. Therefore, the particles are stabilized against aggregation. If some particles aggregates are present before the dilution of the slurry, they are most likely to redisperse after this dilution because of this stabilization. That is why slurry dilution to detect aggregates is incorrect. Other methods are costly because they include testing the slurry by performing CMP processing to determine if the slurry is good. This wastes time, money, and resources. Indeed, performing CMP processing to test a slurry consumes silicon wafers, slurry itself, manpower and time before the acceptance of the slurry. If the slurry has to be discarded, the CMP testing slurry line must be purged and cleaned which represents an additive loss of resources. Therefore, a need exists for a method for testing a slurry prior to a CMP process.

Skilled artisans appreciate that elements in the figures are illustrated for simplicity and clarity and have not necessarily been drawn to scale. For example, the dimensions of some of the elements in the figures may be exaggerated relative to other elements to help improve the understanding of the embodiments of the present invention.

DETAILED DESCRIPTION OF THE PREFERRED EMBODIMENTS

When a slurry manufacturer delivers slurry to a semiconductor manufacturer, the semiconductor manufacturer wants to know that the quality is good. Either the slurry manufacturer or the semiconductor manufacturer can determine the quality. Currently in the semiconductor industry, the slurry manufacturers do not provide suitable assurance of the slurry quality so the semiconductor manufacturer must determine the quality. In addition, no quality tests or method are recommended to the semiconductor manufacturer for testing the slurry. Also, no parameters for acceptable aggregation are provided. An analytical methodology to test slurry for aggregation and to assess if the slurry should be accepted or rejected is discussed herein. An aggregate results from aggregation. Aggregation is the process by which separate colloidal entities like silica particles join together to form a bigger colloidal entity (the aggregate). The aggregate may be reversible and can be redispersed, or irreversible and cannot be redispersed.

Figure 1:
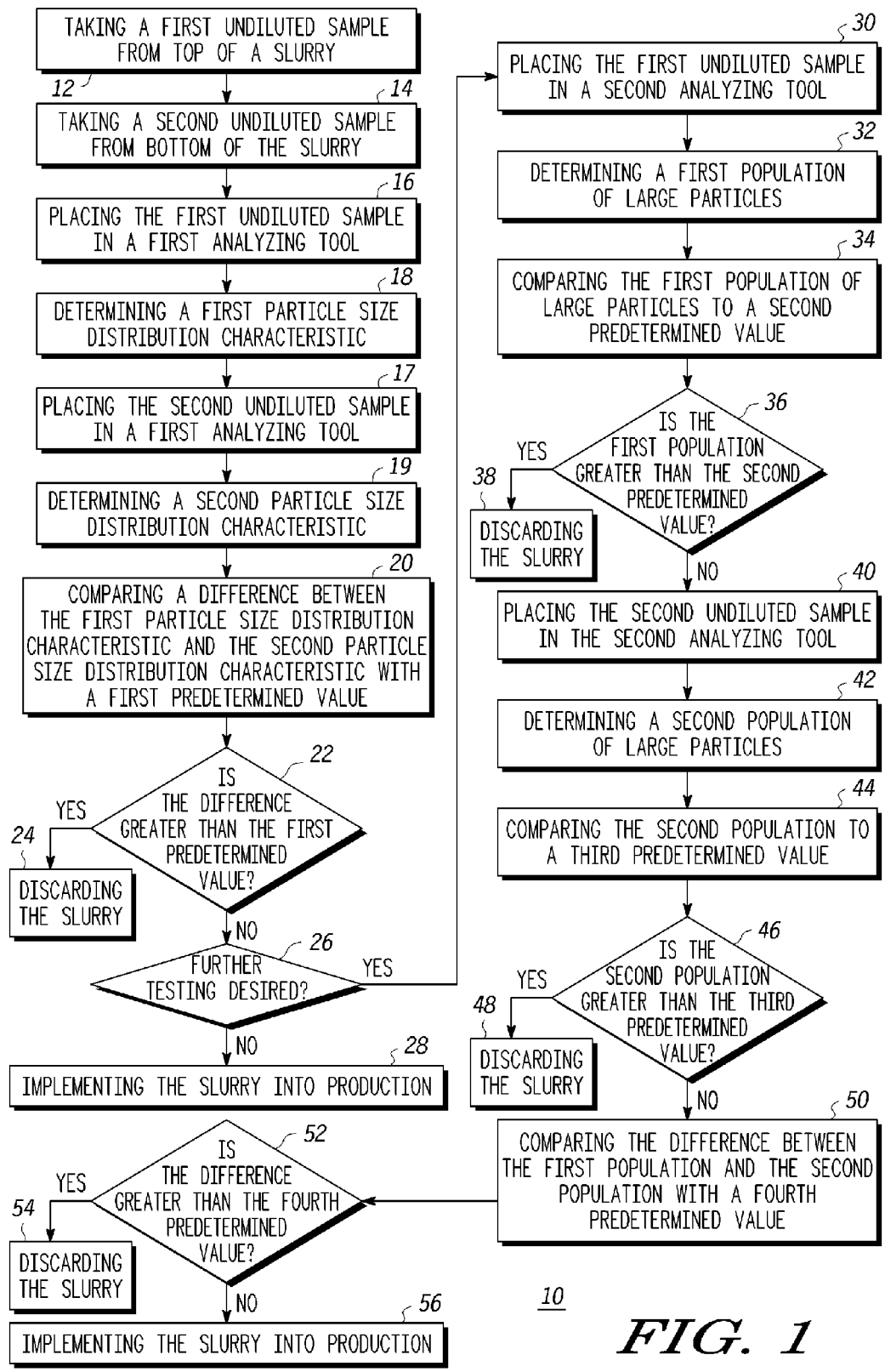
FIG. 1 is a flow used to test a semiconductor device and use a slurry to form a semiconductor device in accordance with one embodiment of the invention, given by way of example.

In one embodiment, the quality of the slurry is determined by acoustic attenuation spectroscopy (AAS). AAS derives the particle size distribution of a sample by measuring viscous, scattering, and diffraction loss of a signal through the slurry. In one embodiment, the Acoustosizer II from Colloidal Dynamics can be used to perform AAS. The Acousosizer II can also be used with the Electrokinetic Sonic Amplitude mode (ESA) instead of the attenuation mode (i.e., AAS). The ESA mode applies a voltage pulse across the sample, causing colloidal particles (which are nearly always electrically charged) to shake backwards and forwards. This motion generates sound waves. The sound waves can be used to across the slurry, which generates sound waves. The sound waves can be used to determine the particle size distribution of the sample. A flow 10, as shown in FIG. 1, that may use MS to determine whether a slurry should be implemented into production and used to form a semiconductor device or should be discarded will be described.

Figure 2:
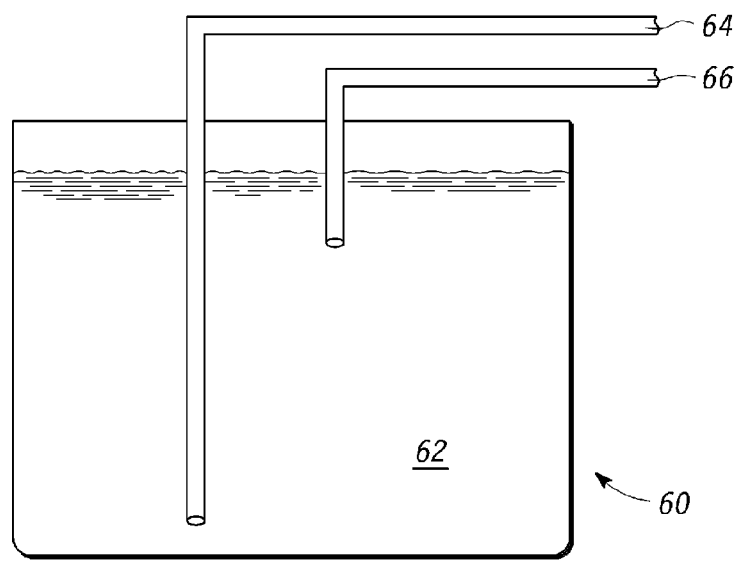
FIG. 2 is a container filled with slurry illustrating from where samples may be taken in accordance with one embodiment of the invention, given by way of example.

Typically, slurry is stored in large containers (e.g., 1000 L), which are sometimes referred to as totes. Shown in FIG. 2, is a container or tote 60 of a slurry 62. The slurry 62 can be any slurry. A first undiluted sample is taken 12 (FIG. 1) from the too of the slurry 62, and a second undiluted sample 62 is taken 14 (FIG. 1) from the bottom of the slurry 62. The first and second undiluted samples are taken without any agitation to the slurry. In other words, the slurry is static when the samples are taken. In one embodiment, any undiluted samples discussed herein may be approximately 100-1000 ml of solution.

After taking 12 the first undiluted sample, the first undiluted sample is placed 16 into a first analyzing tool, which in one embodiment is an AAS tool. The first analyzing tool is used to determine 18 a first particle size distribution characteristic. To determine 18 the first particle size distribution characteristic, a measurement is made using the first analyzing tool. Preferably, the measurement is performed until an acoustic attenuation plot is stable in low frequencies and only the first stable plot is used. The plot may be stable during the first measurement. However, if bubbles are present in the sample, the plot may not be stable during the first measurement. However, the bubbles will disappear after further measurement because during measurement the slurry is flowed through piping in the first analyzing tool and the pressure during the flowing will eliminate bubbles.

The first particle size distribution characteristic can be a measured parameter or a calculation derived from measured parameters. For example, in one embodiment the median size of the particles (d50), the maximum size of 85 percent of the particles (d85), or the maximum size of 15 percent of the particles (d15), is determined by the first analyzing tool or from calculations of data generated by the first analyzing tool. The d50, d85, or d15 parameters each alone may be the first particle size distribution characteristic. Alternatively, any two or more of the parameters may used in a formula. In one embodiment, two of these parameters are subtracted from each other and the difference may be the first particle size distribution characteristic. For example, the first particle size distribution characteristic might be d85-d15.

Figure 3:
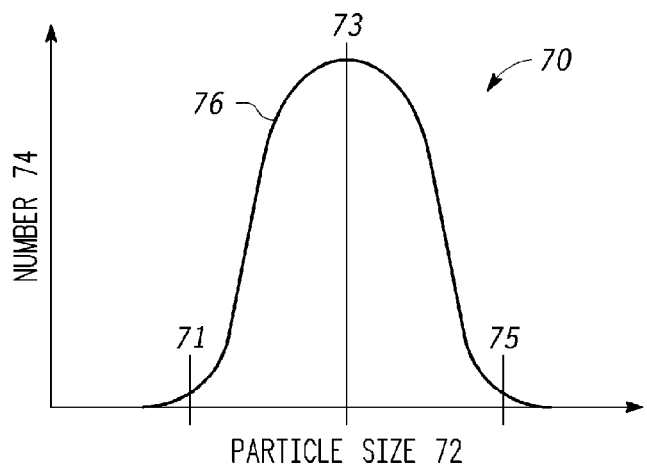
FIG. 3 is a graphical representation of a first particle size distribution in accordance with one embodiment of the invention, given by way of example.

FIG. 3 illustrates an example of graphical representation 70 of a first particle size distribution according to one embodiment. The x-axis 72 is the particle size and the y-axis 74 is the number of particles. As illustrated in FIG. 3, the first particle size distribution curve 76 is a normal distribution. Element 71 marks the d15 parameter, element 73 marks the d50 parameter, and element 75 marks the d85 parameter. Thus, the difference between the d85 parameter 75 and the d15 parameter 71 is the width of the particle size distribution.

After determining 18 the first particle size distribution characteristic, the second undiluted sample from the bottom of the slurry is taken 14 if it wasn't previously taken. In other words, the second undiluted sample can be taken at any time before testing this sample and need not be taken after or immediately after (meaning the next step after) the taking of the first undiluted sample. Then the second undiluted sample is placed 17 into the first analyzing tool. The first analyzing tool is then used to determine 19 a second particle size distribution characteristic, which can be any characteristic previously described for the first particle size distribution characteristic. However, the first particle size distribution characteristic and second particle size distribution characteristic must be the same characteristic although the values of the characteristic may differ. For example, if the first particle size distribution characteristic is only d50, then the second particle size distribution characteristic is also d50 although the values of d50 for the first and second undiluted samples may be different.

As a skilled artisan should recognize, the taking, placing, and determining of the second undiluted sample can be done before these same processes with the first diluted sample.

After determining 18 and 19 the first and second particle size distribution characteristic, the difference between the first particle size distribution characteristic and the second particle size distribution characteristic is calculated. This difference is compared 20 to a first predetermined value. The first predetermined value is a threshold for what is considered a "good" or "bad" slurry.

In one embodiment after comparing 20, a decision 22 is made as to whether or not the difference is greater than the first predetermined value. In another embodiment, the decision 22 could be whether or not the difference is less than the first predetermined value. Using the embodiment illustrated in FIG. 1, if the difference is greater than the first predetermined value then the slurry is discarded 24. If the difference is not greater than the first predetermined value another decision, to be discussed below, is made.

In the embodiment where the difference between d85 and d15 is the first and second particle size distribution characteristics, the first predetermined value may be a value between 1 to 8 nm, or more specifically approximately 4 nm if the slurry used is CUS1351, a barrier slurry from Rohm and Haas Electronic Materials. It is believed that if the difference between the first and second particle distribution characteristics for the first and second undiluted samples is 1 nm or less then the slurry is usable. However, if the difference is 8 nm or greater, then the slurry should be discarded to avoid defectivity problems. In other words, if the particle size distribution between the top and bottom of the slurry is greater than 8 nm then the slurry should not be used, but if the difference is 1 nm or less then the slurry should be used. Instead, if the difference is greater than 1 nm and less than 8 nm, the slurry may or may not be usable. A skilled artisan should recognize that other slurries will have other corresponding decision threshold values. In a preferred embodiment, the difference between the first and second particle size distribution characteristics is zero meaning that the top and the bottom of the slurry have the same particle size distribution. However, the bottom of the slurry is likely to have larger particle size distribution because the small particles will aggregate into larger ones and sediment to the bottom of the slurry.

Figure 4:
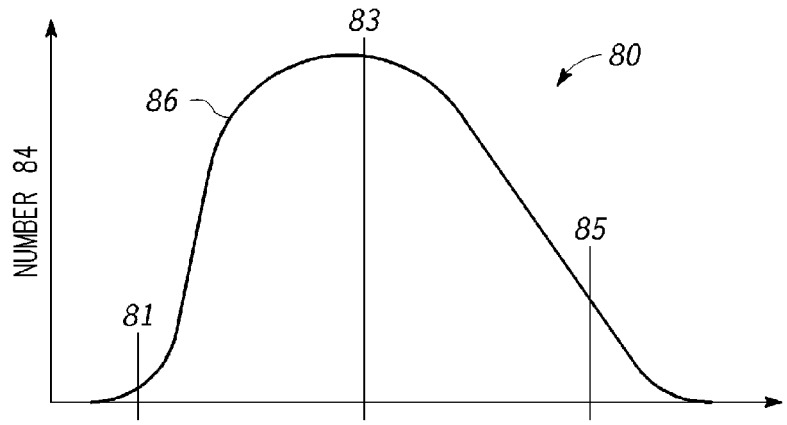
FIG. 4 is a graphical representation of a second particle size distribution in accordance with one embodiment of the invention, given by way of example.

FIG. 4 illustrates an example of a graphical representation 80 of a second particle size distribution according to one embodiment. Element 81 marks the d15 parameter, element 83 marks the d50 parameter and element 85 marks the d85 parameter. The x-axis 82 is the particle size and the y-axis 84 is the number of particles. The curve 86 has a longer tail than the curve 76 and thus has more particles with a larger particle size than the slurry corresponding to curve 76. If the curve 76 of FIG. 3 was the result of the top slurry and the curve 86 of FIG. 4 was the result of the bottom slurry, then it is likely that the slurry would be discarded because the particle size distribution between the top and bottom of the slurry is likely to be too great. In other words, the bottom of the slurry probably has too many large particles, which will create defects if the slurry is used in a CMP process.

By looking at the particle size distribution, sedimentation and aggregation of particles is evaluated. If there is a lot of sedimentation or aggregation of particles, the slurry should be discarded and not implemented into production.

Although only particle size distribution was discussed as a parameter calculated by or from data generated by the first analyzing tool, other parameters can be determined such as pH, temperature, zeta potential, conductivity, and the like. These other parameters can be used to help determine if the slurry should be discarded or implemented into production.

As briefly mentioned above, if the difference is not greater than the first predetermined value another decision 26 is made. The decision 26 is whether or not further testing is desired. In one embodiment, the decision 26 is based on whether there is a concern about many large particles (e.g., greater than 5 microns in diameter) being present in the slurry. If the particle size distribution in the slurry is a bimodal distribution (for example, with modes being one order of magnitude different), the first analyzing tool will not see the bimodal distribution and instead will only report the first mode of particle distribution. Therefore, another tool would be needed to see if a second mode is present. One tool that can be used is the Accusizer FX from Particle Sizing Systems. This tool optically counts and measures particles having diameters from 0.5 to 25 microns. This tool also, as described below, can be used without diluting the slurry to check if the large particles are present or to validate and confirm the results of the first analyzing tool.

If it is decided that further testing is not desired, then the slurry should be implemented 28 into production. However, if further testing is desired, then the first undiluted sample is placed 30 into a second analyzing tool. The first undiluted sample may be the same exact sample used in the first analyzing tool, but instead, it may be another sample taken from the container 60 at the top of the slurry 62 using, in one embodiment, pipe 66. Next, a first population of large particles is determined 32. (If the second analyzing tool is being used to validate the first analyzing tool's data then the first population (and other measurements and values described below) may include all particles and not just large particles.) Large particles are particles larger than approximately 1 micron in diameter or in the range of approximately 1 to 25 microns in diameter. Next, the first population of large particles is compared 34 to a second predetermined value.

In one embodiment after comparing 34 a decision 36 is made as to whether or not the first population is greater than the second predetermined value. In another embodiment, the decision 36 could be whether or not the population is less than the second predetermined value. Using the embodiment illustrated in FIG. 1, if the first population is greater than the first predetermined value then the slurry is discarded 38. If the difference is not greater than the second predetermined value then further testing is performed. In one embodiment, the second predetermined value ranges from 200 to 2000 particles per ml. The particle size considered here can be any size larger than approximately 1 micron.

If the first population is not greater than the second predetermined value, then testing proceeds by placing 40 the second undiluted sample in the second analyzing tool. The second undiluted sample may be the same exact sample used in the first analyzing tool, but instead, it may be another sample taken from the container 60 at the bottom of the slurry 62 using, in one embodiment, pipe 64.

Next, a second population of large particles is determined 42. Again, large particles are particles larger than 5 micron in diameter or in the range of 5 to 25 microns in diameter. Next, the second population of large particles is compared 44 to a third predetermined value.

In one embodiment after comparing 44, a decision 46 is made as to whether or not the first population is greater than the third predetermined value. In another embodiment, the decision 46 could be whether or not the population is less than the third predetermined value. Using the embodiment illustrated in FIG. 1, if the second population is greater than the third predetermined value then the slurry is discarded 48. If the difference is not greater than the third predetermined value, then the flow 10 is continued. In one embodiment, the third predetermined value ranges from approximately 200 to 2000 particles per ml. The particle size considered here can be any size larger than approximately 1 micron.

If the second population is not greater than the third predetermined value, then the flow 10 is continued and the difference between the first population and the second population is calculated to confirm the results of the first analysis tool. This difference is compared 50 with a fourth predetermined value. In one embodiment, the fourth predetermined value ranges from approximately 500 to 10000 particles per ml. The particle size considered here can be any size larger than approximately 1 micron.

In one embodiment after comparing 50, a decision 52 is made as to whether or not the difference is greater than the fourth predetermined value. In another embodiment, the decision 52 could be whether or not the difference is less than the fourth predetermined value. Using the embodiment illustrated in FIG. 1, if the difference is greater than the fourth predetermined value, then the slurry is discarded 54. If the difference is not greater than the fourth predetermined value then the slurry is implemented 56 into production. When a slurry is implemented into production it is hooked up in the production line and used for CMP processing. More specifically, implementing the slurry into production herein includes providing a semiconductor substrate and applying a slurry to the semiconductor substrate.

Figure 5:
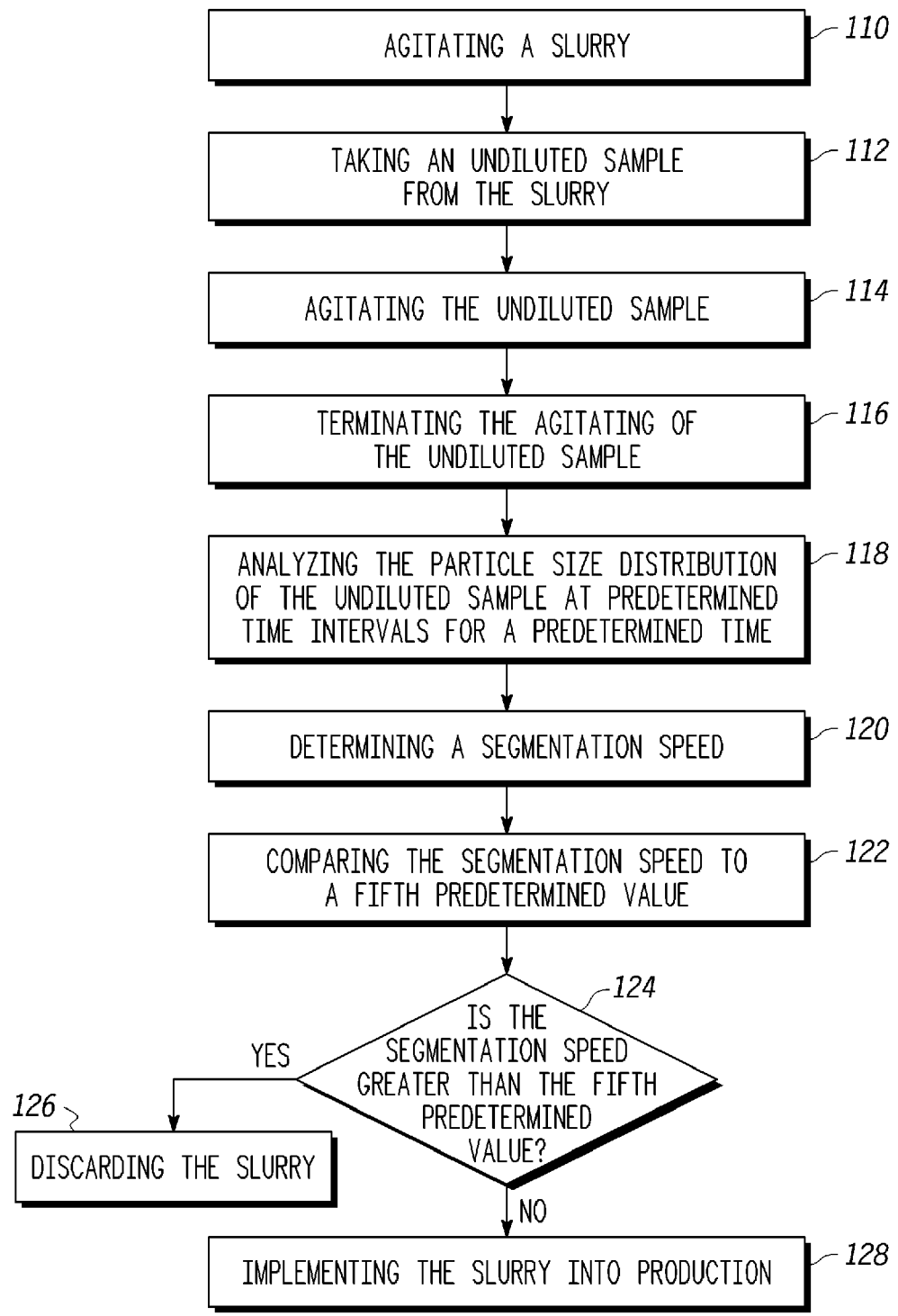
FIG. 5 is another flow used to test a slurry to form a semiconductor device in accordance with one embodiment of the invention, given by way of example.

The second analyzing tool can also be used in a different method to determine if the slurry should be implemented into production or discarded. This method is illustrated in the flow 100 of FIG. 5. The flow 100 can be used as an independent method or with the first analyzing tool. To use the flow 100 with the first analysis tool in one embodiment, if the answer to decision 26 is yes, further testing is desired instead of performing the processes 30-56, the flow 100 can be used. In another embodiment, instead of implementing 56 the slurry, the flow 100 can be used for additional testing.

In the flow 100, the slurry is first agitated 110. This may be performed by agitating the container 60. One way of agitating the container 60 is to hook the container 60 up to the tool used in production and agitate the slurry using the production tool. Alternatively, other methods can be used. In one embodiment, the slurry is agitated 110 in the container 60 for approximately 20 minutes. After agitating 110 the slurry, a third undiluted sample is taken 112 from the slurry. It does not matter from which part of the slurry or container the sample is taken (e.g., the top or bottom) since the slurry is agitated immediately before taking the sample. Due to the agitation the slurry should be homogenous.

Figure 6:
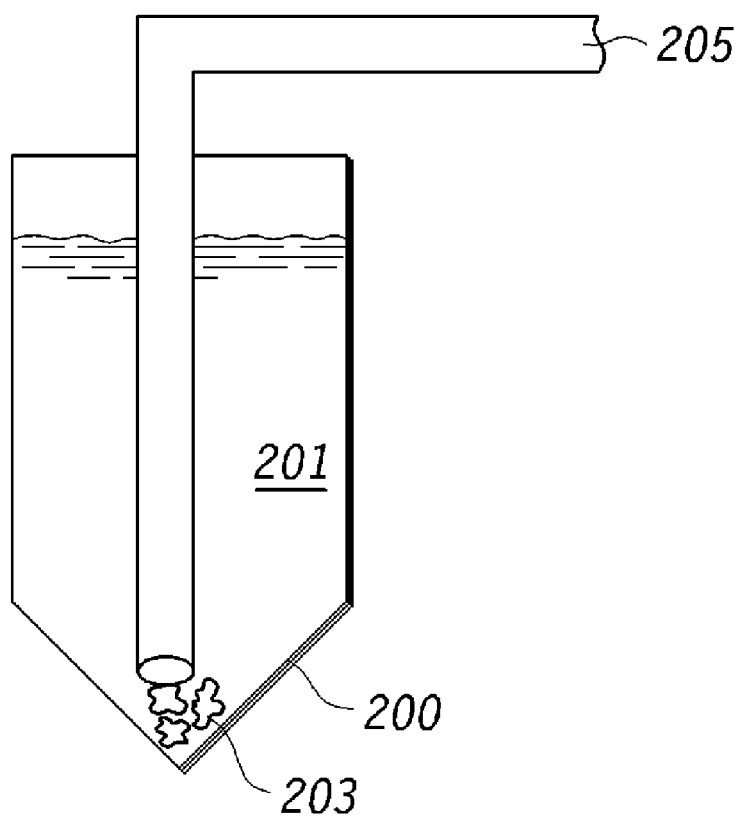
FIG. 6 is an example of a flask used to hold a slurry sample in accordance with the flow of FIG. 5 in accordance with one embodiment of the invention, given by way of example.

The third undiluted sample may be placed in a flask or any type of suitable container. FIG. 6 illustrates an example of a flask 200 that may be used to hold a slurry 201 in one embodiment. This flask 200 has a conical shape and allows for sedimentation 203 to travel to the bottom of the flask and congregate. In one embodiment, the pipe 205 used to take any slurry into the tool can be directed to the bottom of the flask and therefore the any sedimentation, if present, is likely to be detected.

Next, the third undiluted sample is agitated 114 because the sample should be agitated immediately before testing begins. Enough agitation to mix up the sample may be performed. In one embodiment, the sample is agitated for approximately a few seconds to 1 minute. Next, the agitation of the third undiluted sample is terminated 116 and the testing begins. The time delay between the end of agitation and testing should be minimal.

To test the third undiluted sample, the particle size distribution of the third undiluted sample is analyzed 118 at predetermined time intervals for a predetermined time. In one embodiment, the predetermined time intervals are approximately 5 minutes and the predetermined time is approximately 1 hour or less, or more specifically approximately 20 minutes. This analysis 118 is a sequential sedimentation test taken at the predetermined time intervals. The particle size distribution at the bottom of the flask is analyzed at each predetermined time interval to see if sedimentation is occurring.

Based on the analyzing 118, the sedimentation speed of the third undiluted sample is determined 120 for a given particle size. This can be performed by looking at the particle size distribution for each measurement. In one embodiment, the sedimentation speed of particles with diameters between 1 to 5 microns is analyzed. In another embodiment, particles having diameters of approximately 15 microns are found in the slurry and thus, the sedimentation speed of these particles is also considered. If aggregation or sedimentation occurs, the particles size distribution will show an increased number of large particles.

After determining the sedimentation speed 120, the sedimentation speed is compared 122 to a fifth predetermined value. After comparing, a decision 124 is made as to whether or not the sedimentation speed is greater than the fifth predetermined value in one embodiment. In another embodiment, the decision 124 could be whether or not the sedimentation speed is less than the fifth predetermined value. Using the embodiment illustrated in FIG. 5, if the difference is greater than the fifth predetermined value, then the slurry is discarded 126. If the difference is not greater than the fourth predetermined value then the slurry is implemented 128 into production. In one embodiment, the fifth predetermined value is approximately 20 to 200 particles per ml per minute. A slurry that is suitable for use in production will have a slow sedimentation speed, such as a speed less than approximately 20 particles per ml per minute. However, a slurry that should be disposed of will have a fast sedimentation speed, such as a speed greater than approximately 200 particles per ml per minute.

By now it should be appreciated that there has been provided a method for testing a slurry used to form a semiconductor device. The method can be performed prior to CMP processing and is more reliable than prior art testing because it tests undiluted slurry samples.

In the foregoing specification, the invention has been described with reference to specific embodiments. However, one of ordinary skill in the art appreciates that various modifications and changes can be made without departing from the scope of the present invention as set forth in the claims below. Accordingly, the specification and figures are to be regarded in an illustrative rather than a restrictive sense, and all such modifications are intended to be included within the scope of the present invention.

Benefits, other advantages, and solutions to problems have been described above with regard to specific embodiments. However, the benefits, advantages, solutions to problems, and any element(s) that may cause any benefit, advantage, or solution to occur or become more pronounced are not to be construed as a critical, required, or essential feature or element of any or all the claims. As used herein, the terms "comprises," "comprising," or any other variation thereof, are intended to cover a non-exclusive inclusion, such that a process, method, article, or apparatus that comprises a list of elements does not include only those elements but may include other elements not expressly listed or inherent to such process, method, article, or apparatus. The terms "a" or "an", as used herein, are defined as one or more than one.

The invention claimed is:

1. A method for forming a semiconductor device, the method comprising:
    applying a slurry to the semiconductor substrate, wherein the slurry was tested using a testing method, the test method comprising:
    taking a first undiluted sample from a top of the slurry;
    determining a first particle size distribution characteristic of the first undiluted sample;
    taking a second undiluted sample from a bottom of the slurry;
    determining a second particle size distribution characteristic of the second undiluted sample; and
    comparing a difference between the first particle size distribution characteristic and the second particle size distribution characteristic with a first predetermined value.

2. The method as claimed in claim 1, wherein the testing method further includes discarding the slurry based on the step of comparing.

3. The method as claimed in claim 1, wherein the testing method further includes implementing the slurry into a production line after the step of comparing.

4. The method as claimed in claim 1, wherein determining the first particle size distribution characteristic includes measuring the first particle size distribution characteristic by acoustic attenuation spectroscopy.

5. The method as claimed in claim 1, wherein determining the first particle size distribution characteristic includes measuring the first particle size distribution characteristic by electrokinetic sonic amplitude.

6. The method as claimed in claim 1, wherein the testing method further includes determining a first population of large particles of the first undiluted sample; and comparing the first population of large particles to a first threshold.

7. The method as claimed in claim 6, wherein the testing method further includes discarding the slurry based on the step of comparing.

8. The method as claimed in claim 6, wherein the testing method, further includes implementing the slurry into a production line after the step of comparing.

9. The method as claimed in claim 6, wherein the testing method further includes determining a second population of large particles of the second undiluted sample; and comparing the second population of large particles to a second threshold.

10. The method as claimed in claim 3, wherein the testing method further includes discarding the slurry based on the step of comparing.

11. The method as claimed in claim 9, wherein the testing method, further includes implementing the slurry into a production line after the step of comparing.

12. The method as claimed in claim 9, wherein the testing method further includes comparing the difference between the first population of large particles and the second population of large particles with a second predetermined value.

13. The method as claimed in claim 12, wherein the testing method further includes discarding the slurry based on the step of comparing.

14. The method as claimed in claim 12, wherein the testing method, further includes implementing the slurry into a production line after the step of comparing.

15. A method for testing a slurry, the method comprising:
    taking a first undiluted sample from a top of the slurry;
    determining a first particle size distribution characteristic of the first undiluted sample;
    taking a second undiluted sample from a bottom of the slurry;
    determining a second particle size distribution characteristic of the second undiluted sample; and
    comparing a difference between the first particle size distribution characteristic and the second particle size distribution characteristic with the first predetermined value.

16. The method as claimed in claim 15, wherein the method further includes determining a first population of large particles of the first undiluted sample; and
    comparing the first population of large particles to a first threshold.

17. The method as claimed in claim 15, wherein determining the first particle size distribution characteristic includes measuring the first particle size distribution characteristic by acoustic attenuation spectroscopy.

18. The method as claimed in claim 15, the method further comprising:

agitating the slurry after comparing the difference between the first particle size distribution characteristic and the second particles size distribution characteristic with the first predetermined value;
taking a sample from the slurry in a flask after agitating the slurry;
agitating the flask;
analyzing the particle size distribution at predetermined time intervals for a predetermined time after agitating the flask;
determining a sedimentation speed of the sample; and
comparing the sedimentation speed to a predetermined threshold.

19. The method as claimed in claim 18, wherein the flask comprises a conical shape.

20. A method for testing a slurry, the method comprising:
taking a first undiluted sample from a top of the slurry;
determining a first particle size distribution characteristic of the first undiluted sample using an acoustic signal;
taking a second undiluted sample from a bottom of the slurry;
determining a second particle size distribution characteristic of the second undiluted sample using an acoustic signal;
comparing a difference between the first particle size distribution characteristic and the second particle size distribution characteristic with the first predetermined value; and
implementing the slurry into a production line based on the comparing.

* * * * *

UNITED STATES PATENT AND TRADEMARK OFFICE
CERTIFICATE OF CORRECTION

| | | |
|---|---|---|
| PATENT NO. | : 8,061,185 B2 | Page 1 of 1 |
| APPLICATION NO. | : 12/091693 | |
| DATED | : November 22, 2011 | |
| INVENTOR(S) | : Philippe Monnoyer et al. | |

It is certified that error appears in the above-identified patent and that said Letters Patent is hereby corrected as shown below:

Column 8, Line 28, please change "as claimed in claim 3," to --as claimed in claim 9,--

Signed and Sealed this

Seventh Day of February, 2012

David J. Kappos
*Director of the United States Patent and Trademark Office*